United States Patent
Nelson

(10) Patent No.: US 6,417,177 B1
(45) Date of Patent: Jul. 9, 2002

(54) CHLOROQUINE DERIVATIVES FOR THE TREATMENT OF PARKINSON'S DISEASE

(75) Inventor: Jodi Nelson, Denver, CO (US)

(73) Assignee: Alpha Research Group, LLC, Reno, NV (US)

( * ) Notice: Subject to any disclaimer, the term of this patent is extended or adjusted under 35 U.S.C. 154(b) by 0 days.

(21) Appl. No.: 09/615,639

(22) Filed: Jul. 13, 2000

Related U.S. Application Data

(60) Provisional application No. 60/202,140, filed on May 5, 2000, provisional application No. 60/175,051, filed on Jan. 7, 2000, and provisional application No. 60/143,767, filed on Jul. 13, 1999.

(51) Int. Cl.$^7$ .......................... A61K 31/47; A61P 25/16
(52) U.S. Cl. .............................. 514/82; 514/7; 514/105
(58) Field of Search .............................. 514/82, 7, 297, 514/313, 311, 105

(56) References Cited

U.S. PATENT DOCUMENTS

| | | | |
|---|---|---|---|
| 4,421,920 A | 12/1983 | Baudouin et al. | 546/163 |
| 5,154,924 A | 10/1992 | Friden | 424/85.91 |
| 5,210,076 A | 5/1993 | Berliner et al. | 514/21 |
| 5,430,039 A | 7/1995 | Roberts-Lewis et al. | 514/297 |
| 5,596,002 A | 1/1997 | Hofheinz et al. | 514/313 |
| 5,624,938 A | 4/1997 | Pernis | 514/313 |
| 5,639,737 A | 6/1997 | Rubin | 514/53 |
| 5,736,556 A | 4/1998 | Moldt et al. | 514/304 |
| 5,834,505 A | 11/1998 | Peters | 514/454 |
| 5,948,791 A | 9/1999 | Hofheinz et al. | 514/313 |
| 6,015,555 A | 1/2000 | Friden | 424/133.1 |

OTHER PUBLICATIONS

Webser et lal. Biochem Pharmacol 1991, vol. 42, pp. S225–7. Antimalarial activity of optical isomers of quinacrine dihydrochloride against chloroquine–sensitive and resisitant plasmodium faciparum in vitro.*

Haberkorn A et al. Tropenmed Parasitol. 1979, vol. 30, pp. 308–312. Antimalrail activity of the optical isomers of chloroquine diphosphate.*

Ambrozi et al., (1976) "L–Dopa and (–)–deprenil in the treatment of Parkinson's desease: long–term study," Br. J. Pharmacol., 58(3):423–424, Database CA on STN. Chem. Abstr., vol. 86 (Columbus, OH, USA), abstract No. 133721.

Golbe et al., (1993) "Vitamin E and Parkinson's disease," Vitam. E Health Dis., Packer et al Eds., Dekker, New Yourk, NY, pp. 787–797, Database CA on STN. Chem. Abstr., vol. 119, (Columbus, OH, USA), abstract No. 71356.

Hemmer et al., (1967) "Cerebral activity of an herbal preparation (Tebonin) from Ginko biloba," Arzneim.–Forsch., 17(4):491–493, Database CA on STN. Chem. Abstr., vol. 67 (Columbus, OH, USA), abstract No. 52644.

Aisen, Paul S. (1997) "Inflammation and Alzheimer's Disease: Mechanisms and Therapeutic Strategies," Gerontology 43:143–149.

Bhatia, M.S. (1991), "Chloroquine–induced psychiatric complications," British Journal of Psychiatry 159(Nov.):735 (Abstract).

Bhatia, M.S. et al. (1988), "Capgras syndrome in chloroquine induced psychosis," Indian Journal of Psychiatry 30(3):311–313 (Abstract).

Cockroft, K M. et al. (1996) "Cerebroprotective effects of aminoquanidine in a rodent model of stroke," Stroke 27(8):1393–1398.

Conference Proceedings, Stroke Drug Development: Bridging the Gab From Animal Research to Human Trials, Mar. 6–7, 1999, Orlando, FL, Proceedings Transcripts, Side 2, #10.

Donatelli, P. et al. (1994) "Stereoselective inhibition by chloroquine of histamine N–methyltransferase in the human liver and brain," Eur. J. Clin. Pharmacol. 47:345–349.

Feuerstein, G.Z. and Wang, X. (2000) "Animal models of stroke," Molecular Medicine Today 6:133–135.

Garg, P. et al. (1990) "Toxic psychosis due to chloroquine— not uncommon in children," Clinical Pediatrics 29(8):448–450.

Golden, G.T. (1992) "Systemic chloroquine protects against striatal dopamine depleciton induced by unilateral intra–nigral MPP+ injection in rats," Soc. Neurosci., (Abstract); letter from Dr. G.M. Alexander in regard thereto.

Good, M.I. and Shader, R.I. (1997) "Behavioral toxicity and equivocal suicide associated with chloroquine and its derivatives," Am. J. Psychiatry 134(7):798–801.

Good, M.I. and Shader, R.I.(1982) "Lethality and behavioral side effects of chloroquine," J. Clin. Psychopharmacology 2:40–46.

Hagihara, N. et al. (2000) "Vascular protection by chloroquine during brain tumor therapy with Tf–CRM107," Cancer Res. 60:230–234.

Lovestone, S. (1991), "Chloroquine–induced mania," British Journal of Psychiatry 159(Jul):164–165 (Abstract).

Lowrey, A.H. et al., (1997) "Modeling Drug–melanin Interaction with Theoretical Linear Solvation Energy Relationships," Pigment Cell Res. 10 251–256.

(List continued on next page.)

Primary Examiner—Gary L. Kunz
Assistant Examiner—Sarada C Parasad
(74) Attorney, Agent, or Firm—Greenlee, Winner and Sullivan, P.C.

(57) ABSTRACT

This invention provides compositions and methods for increasing cellular respiration of melanized catecholamine neurons, and methods for alleviating symptoms or stopping appearance and/or progression of symptoms of Parkinson's Disease, and methods for preventing symptoms of on-off syndrome associated with treatment with dopamine or a dopamine agonist of a patient suffering symptoms of a disease selected from the group consisting of idiopathic and atypical Parkinson's disease, conditions characterized by nigrostriatal degeneration and multiple system atrophy, said methods comprising administering to said patient an effective amount of a neuromelanin-binding composition having a quinoline ring in a suitable pharmaceutical carrier. Preferably the composition comprises (–)-chloroquine.

17 Claims, No Drawings

OTHER PUBLICATIONS

Ofori–Adjei, D. et al. (1986) "Enantioselective analysis of chloroquine and desethylchloroquine after oral administration of racemic chloroquine," *Therapeutic Drug Monitoring* 8:457–461.

Ofori–Adjei, D. et al. (1986) "Protein binding of chloroquine enantiomers and desethyl–chloroquine," *Br. J. Clin. Pharmac.* 22:356–358.

Rosner, P.I. and Legros, J. (1967) "Hydroxychloroquine et resistance corticale a l'anoxie asphyxique," *Therapie* XXII:355–360.

Sharma, O.P. (1988) "Effectiveness of chloroquine and hydroxychloroquine in treating selected patients with sarcoidosis with neurological involvement," *Archives of Neurology* 55(9):1248–1254.

Shields, D.C. et al., (1999) "A putative mechanism of demyelination in multiple sclerosis by proteolytic enzyme, calpain,"*Proc. Natl. Acad. Sci. USA* 96:11486–11491.

Tedeschi, M. (1983), "A case of acute psychosis due to Chloroquine," *Information Psychiatrique* 59(9):1191–1197 (Abstract).

Webster, R. V. et al. (1991) "Antimalarial activity of optical isomers of quinacrine dihydrochloride against chloroquine–sensitive and –resistant *Plasmodium falciparum* in vitro," *Biochem. Pharm.* 42:S225–S227.

Montastruc JL, 1991. Therapie, 46(4):293–303. recent advances in the clinical pharmacology of parkinsons's disease.*

Lowrey BS, 1997, Pigment Cell Res. vol. 10(5):251–256. Modeling Drug–melanin interaction with theoretical linear solvation energy relationships.*

Paramar RC et al. 2000, J Postgrad Med. 46(1):29–30. Chloroquine induced parkinsonism.*

Abiose, A.K. et al., "Chloroquine–induced venodilation in human hand veins," (1997) *Clin. Pharm. & Therapeutics* 61(6):677–683.

Antonini, A. et al., "Differential diagnosis of Parkinsonism with [$^{18}$F]Fluorodeoxyglucose and PET," (1998) *Movement Disorders* 13(2):268–274.

Ardueser, G.A. and Heim, H.C., "Some effects of chloroquine on oxidative processes in rat heart," (1967) *J. Pharmaceutical Sciences* 56(2):254–258.

Baltzan, M. et al., "Randomized trial of prolonged chloroquine therapy in advanced pulmonary sarcoidosis," (1999) *Am. J. Respir. Crit. Care Med.* 160:192–197.

Behl, C. et al., "Hydrogen peroxide mediates amyloid β protein toxicity," (1994) *Cell* 77:817–827.

Ben–Shachar, D. and Youdim, M.B.H., "Selectivity of melaninized nigra–striatal dopamine neurons to degeneration in Parkinson's disease may depend on iron–melanin interaction," (1990) *J. Neural Transm.* 29:251–258.

Ben–Shachar, D. et al., "The iron chelator desferrioxamine (Desferal) retards 6–hydroxydopamine–induced degeneration of nigrostriatal dopamine neurons," (1991) *J. Neurochemistry* 56(4):1441–1444.

Bergendi, L'. et al., "Chemistry, physiology and pathology of free radicals," (1999) *Life Sciences* 64(18–19):1865–1874.

Bitonti, A.J. et al., "Reversal of chloroquine resistance in malaria parasite plasmodium falciparum by desipramine," (1988) *Science* 241:1301–1303.

Booji, J. et al., "[$^{123}$I]FP–CIT SPECT shows a pronounced decline of striatal dopamine transporter labelling in early and advanced Parkinson's disease," (1997) *J. Neurol. Neurosurg. Psychiatry* 62:133–140.

Bowen, B.C. et al., "Proton MR spectroscopy of the brain in 14 patients with Parkinson's disease," (1995) *Am. J. Neuroradiology* 161(1):61–68.

Burke, R.E., "Programmed cell death and Parkinson's disease," (1998) *Movement Disorders* 13(S1):17–23.

Byrd, T.F. and Horowitz, M.A., "Chloroquine inhibits the intracellular multiplication of *Legionella pneumophila* by limiting the availability of iron. A potential new mechanism for the therapeutic effect of chloroquine against intracellular pathogens," (1991) *J. Clin. Investigation* 88(1);351–357.

Carlsson, Arvid, "Development of new pharmacological approaches in Parkinson's disease," (1986) *Advances in Neurology* 45:513–518.

Chan, P.C. and Bielski, B.H., "Enzyme–catalyzed free radical reactions with nicotinamide adenine nucleotides. II. Lactate dehydrogenase–catalyzed oxidation of reduced nicotinamide adenine dinucleotide by superoxide radicals generated by xanthine oxidase," (1974) *J. Biol. Chem.* 249(4):1317–1319.

Cho, Y.W. and Aviado, D.M., "Pathologic physiology and chemotherapy of plasmodium berghei. IV. Influence of chloroquine on oxygen uptake of red blood cells infected with sensitive or resistant strains," (1968) *Exp. Parasitology* 23(2):143–150.

Chrichton, R.R. and Ward, R.J., "Iron metabolism—new perspectives in view," (1992) *Biochemistry* 31(46):11255–11264.

Chrischilles, E.A. et al., "The health burdens of Parkinson's disease," (1998) *Movement Disorders* 13(3):406–413.

Cotzias, G.C. et al., "Melanogenesis and extrapyramidal diseases," (1964) *Chemistry in Medicine* 23:713–718.

Culvenor, J.G. et al., "Non–Aβ component of Alzheimer's disease amyloid (NAC) revisited," (1999) *Am. J. Pathology* 155:1173–1181.

Cummings, J.L., "Depression and Parkinson's Disease: A Review," (1992) *Am. J. Psychiatry* 149(4):443–454.

Dailly, E. et al., "Chain–breaking antioxidants and ferri–heme–bound drugs are synergistic inhibitors of erythrocyte membrane peroxidation," (1998) *Free Radical. Res.* 28(2):205–214.

D'Amato, R.J. et al., "Selectivity of the Parkinsonian neurotoxin MPTP: toxic metabolite MPP$^+$ binds to neuromelanin," (1986) *Science* 231:987–989.

D'Amato, R.J. et al., "Evidence for neuromelanin involvement in MPTP–induced neurotoxicity," (1987) *Nature* 327:324–326.

Davison, A.J. and Gee, P., "Redox state of cytochrome C in the presence of the 6–hydroxydopamine/oxygen couple: oscillations dependent on the presence of hydrogen peroxide or superoxide," (1984) *Arch. Biochem. and Biophysics* 233(2):761–771.

Debing, I. et al., "Melanosome binding and oxidation–reduction properties of synthetic L–dopa–melanin as in vitro tests for drug toxicity," (1988) *Mol. Pharmacology* 33(4):470–476.

De Duve, C. et al., "Lysosomotropic agents," (1974) *Biochem. Pharm.* 23:2495–2531.

Deepalakshmi, P.D. et al., "Effect of chloroquine on rat liver mitochondria," (1994) *Indian J. Exp. Biology* 32(11):797–799.

De Feo, P. et al., "Chloroquine reduces whole body proteolysis in humans," (1994) *Am. J. Physiology* 267:E183–E186.

Dethy, S. et al., "Asymmetry of basal ganglia glucose metabolism and dopa responsiveness in Parkinsonism," (1998) *Movement Disorders* 13(2):275–280.

Dexter, D.T. et al., "Basal lipid peroxidation in substantia nigra is increased in Parkinson's disease," (1989) *J. Neurochem.* 42(2):381–389.

Di Monte, D.A. et al., "Astrocytes as the site for bioactivation of neurotoxins," (1996) *NeuroToxicology* 17(3–4):697–704.

Farid, M.A., "The malaria campaign—why not eradication?" (1998) *World Health Forum* 19:417–427.

Fridovich, I., "Superoxide dismutases," (1975) 147–159.

Fukushima, T. et al., "Radical formation site of cerebral complex I and Parkinson's disease," (1995) *J. Neuroscience Res.* 42:385–390.

German, D.C. et al., "1–methyl–4–phenyl–1,2,3,6–tetra–hydropyridine–induced Parkinsonian syndrome in macaca faxcicularis: which midbrain dopaminergic neurons are lost?" (1988) *Neuroscience* 24(1):161–174.

Ghigo, D. et al., "Chloroquine stimulates nitric oxide synthesis in murine, porcine, and human endothelial cells," (1998) *J. Clin. Invest.* 102(3):595–605.

Gibbs, W.R.G. and Lees, A.J., "Anatomy, pigmentation, ventral and dorsal subpopulations of the substantia nigra, and differential cell death in Parkinson's disease," (1991) *J. Neurology, Neurosurgery, and Psychiatry* 54:388–396.

Glinka, Y.Y. and Youdim, M.B.H., "Inhibition of mitochondrial complexes I and IV by 6–hydroxydopamine," (1995) *Eur. J. Pharmacology Environ. Toxicol. Pharmacol. Section* 292, 329–332.

Glinka, Y. et al., "Nature of inhibition of mitochondrial respiratory complex I by 6–hydroxydopamine," (1996) *J. Neurochemistry* 66(5):2004–2010.

Golbe, L.I., "Alpha–synuclein and Parkinson's disease," (1999) *Movement Disorders* 14(1):6–9.

Goldstein, M. and Lieberman, A., "The role of the regulatory enzymes of catecholamine synthesis in Parkinson's disease," (1992) *Neurology* 42(S4):8–12.

Gotham, A.M. et al., "Levodopa treatment may benefit or impair 'frontal' function in Parkinson's disease," (1986) *Lancet* 25;2(8513):970–971.

Graham, D., "Catecholamine toxicity: A proposal for the molecular pathogenesis of manganese neurotoxicity and Parkinson's diseae," (1984) *Toxicology* 5(1):83–96.

Graham, D.G., "Oxidative pathways for catecholamines in the genesis of neuromelanin and cytotoxic quinones," (1978) *Molecular Pharmacology* 14:633–643.

Graham, D.G., "Autoxidation versus covalent binding of quinones as the mechanism of toxicity of dopamine, 6–hydroxydopamine, and related compounds toward C1300 neuroblastoma cells in vitro" (1978) *Molecular Pharmacology* 14:644–653.

Hall, S. et al., "MRI, brain iron and experimental Parkinson's disease," (1992) *J. Neurological Sci.* 198–208.

Hirsch, E. et al., "Melanized dopaminergic neurons are differentially susceptible to degeneration in Parkinson's disease," (1988) *Nature* 334:345–348.

Hirsch, E.C. and Faucheux, B.A., "Iron metabolism and Parkinson's disease," (1998) *Movement Disorders* 13(S1):39–45.

Ivanina, T.A. et al., "A study of the mechanisms of chloroquine retinopathy," (1989) *Ophthalmic Res.* 21:216–220.

Ivanova, S. et al., "Cerebral ischemia enhances polyamine oxidation: identification of enzymatically formed 3–aminopropanal as an endogenous mediator of neuronal and glial cell death," (1998) *J. Exp. Med.* 188(2):327–340.

Jackson, M.J. et al., "Inhibition of lipid peroxidation in muscle homogenates by phospholipase A2 inhibitors," (1984) *Bioscience Reports* 4(7):581–587 (abstract only).

Jenner, P., "Oxidative stress in Parkinson's disease and other neurodegenerative disorders," (1996) *Pathologie Biologie* 44(1):57–64.

Jenner, P. et al., "Understanding cell death in Parkinson's disease," (1998) *Annals of Neurology* 44(1):S72–S84.

Karmazyn, M. et al., "The mechanism of coronary artery spasm: roles of oxygen, prostaglandins, sex hormones and smoking," (1979) *Medical Hypothesis* 5:447–452.

Kienzl, E. et al., "Iron as catalyst for oxidative stress in the pathogenesis of Parkinson's disease?" (1999) *Life Sci* 65(18–19):1973–1976.

Koller, W.C., "When does Parkinson's disease begin?", (1992) *Neurology* 42(S4):27–31.

Krogstad, D.J. and Schlesinger, P.H., "Acid–vesicle function, intracellular pathogens, and the action of chloroquine against *plasmodium falciparum*," (1987) *N.E. J. Med.* 317(9):543–549.

Langston, J.W. et al., "Pargyline prevents MPTP–induced Parkinsonism in primates," (1984) *Science* 225:1480–1482.

Langston, J.W., "MPTP neurotoxicity: an overview and characterization of phases of toxicity," (1985) *Life Sciences* 36:201–206.

Larsson, B. and Tjälve, H., "Studies on the mechanism of drug–binding to melanin," (1979) *Chemical Pharmacology* 28:1181–1187.

Leahy, F. et al., "Desquamative interstitial pneumonia responsive to chloroquine," (1985) *Clinical Pediatrics* 24(4):230–232.

Legssyer, R. et al., "Effect of chronic chloroquine administration on iron loading in the liver and reticuloendothelial system and on oxidative responses by the alveolar macrophages," (1999) *Biochem. Pharmacology* 57(8):907–911.

Lieberman et al., "Does selegiline provide a symptomatic or a neuroprotective effect?", (1992) *Neurology* 42(S4):41–48.

Lin, A.M–Y et al., "Striatal dopamine dynamics are altered following an intranigral infusion of iron in adult rats," (1998) *Free Radical Biology & Medicine* 24(6):988–993.

Linnik, M.D. et al., "Evidence supporting a role for programmed cell death in focal cerebral ischemia in rats," (1993) *Stroke* 24(12):2002–2009.

Loo, D.T. et al., "Apoptosis is induced by β–amyloid in cultured central nervous system neurons," (1993) *Proc. Natl. Acad. Sci. USA* 90:7951–7955.

Lyden, A. et al., "Studies on the melanin affinity of haloperidol," (1982) *Arch. Int. Pharmacodyn. Ther.* 259(2):230–243.

Magwere, T. et al., "Effects of chloroquine treatment on antioxidant enzymes in rat liver and kidney," (1997) *Free Radical Biology & Medicine* 22(1–2):321–327.

Makarenko, I.E. and Levitsky, E.P., "Resoquin in the clinic of internal illnesses, and the possible side effects of its use," (1950).

Maret, G. et al., "The MPTP story: MAO activates tetrahydropyridine derivatives to toxins causing Parkinsonism," (1990) *Drug Metabolism Reviews* 22(4):291–332.

Martin, W.R.W. et al., "Increasing striatal iron content associated with normal aging," (1998) *Movement Disorders* 13(2):281–286.

Matsubara, K. et al., "Beta–carbolinium cations, endogenous $MPP^+$ analogs, in the lumbar cerebrospinal fluid of patients with Parkinson's," (1995) *Neurology* 45(12):2240–2245.

Meerson, F.Z. et al., "Prevention of stress disorders of myocardial contractile function using membrane protectors," (1983) *Kardiologiia* 23(7):86–90 (abstract and translation in English).

Mena, M.A., "Pharmacokinetics of L–DOPA in patients with Parkinson's Disease," (1986) *Advances in Neurology* 45:481–486.

Merad–Boudia, M. et al., "Mitochondrial impairment as an early event in the process of apoptosis induced by glutathione depletion in neuronal cells: relevance to Parkinson's disease," (1998) *Biochem. Pharmacology* 56:645–655.

Mielke, J.G. et al., "Chloroquine administration in mice increases beta–amyloid immunoreactivity and attenuates kainate–induced blood–brain barrier dysfunction," (1997) *Neuroscience Lett.* 227(3):169–172.

Minotti, G. and Aust, S.D., "The requirement for iron (III) in the initiation of lipid peroxidation by iron (II) and hydrogen peroxide," (1987) *J. Biological Chemistry* 262(3):1–98–1104.

Mizuno, Y. et al., "Mitochondrial dysfunction in Parkinson's disease," (1998) *Annals of Neurology* 44(S1):S99–S109.

Monteiro, H.P. and Winterbourn, C.C., "6–hydroxydopamine releases iron from ferritin and promotes ferritin–dependent lipid peroxidation," (1989) *Biochem. Pharm.* 38(23):4177–4182.

Mytilineou, C. et al., "L–(–)–desmethylselegiline, a metabolite of selegiline [L0(–)–deprenyl], protects mesencephalic dopamine neurons from excitotixicity in vitro," (1997) *J. Neurochemistry* 68(1):434–436.

Navas, P. et al., "Decrease of NADH in HeLa cells in the presence of transferrin or ferricyanide," (1986) *Biochem. and Biophys. Res. Communications* 135(1):110–115.

Nicklas, W.J. et al., "Inhibition of NADH–linked oxidation in brain mitochondria by 1–methyl–4–phenyl–pyridine, a metabolite of the neurotoxin, 1–methyl–4–phenyl–1,2,5,6–tetrahydropyridine," (1985) *Life Sciences* 36:2503–2508.

Okamoto, M. et al., "Internucleosomal–DNA cleavage involved in ischemia–induced neuronal death," (1993) *Biochem. and Biophys. Res. Communications* 196(3):1356–1362.

Octave, J–N et al., "Iron uptake and utilization by mammalian cells. I: Cellular uptake of transferrin and iron," (1983) *TIBS* 217–220.

Olanow, C.W. and Calne, D., "Does selegiline monotherapyin Parkinson's disease act by symptomatic or protective mechanisms?" (1992) *Neurology* 42(S4):13–26.

Ornstein, M.H. and Sperber, K., "The antiinflammatory and antiviral effects of hydroxychloroquine in two patients with acquired immunodeficiency syndrome and active inflammatory arthrtitis," (1996) *Arthritis Rheum.* 39(1):157–161.

Poewe, W.H. and Wenning, G.K., "The natural history of Parkinson's disease," (1998) *Annals of Neurology* 44(S1):S1–S9.

Pratt, W.B. and Fekety, R., "Chemotherapy of malaria," *The Antimicrobial Drugs*, (1986) Oxford University Press, New York, Chapter 14:355–384.

Remblier, C. et al., "Lactic acid–induced increase of extracellular dopamine measured by microdialysis in rat striatum: evidence for glutamatergic and oxidative mechanisms," (1999) *Brain Research* 837:22–28.

Riederer, P. et al., "Transition metals, ferritin, glutathione, and ascorbic acid in Parkinsonian brains," (1989) *J. Neurochemistry* 52(2):515–520.

Rollema, H. et al., "In vivo intracerebral microdialysis studies in rats of $MPP^+$ analogues and related charged species," (1990) *J. Med. Chem.* 33:221–2230.

Rollema, H. et al., "$MPP^+$–like neurotoxicity of a pyridinium metabolite derived from haloperidol: In vivo microdialysis and in vitro mitochondrial studies," (1994) *J. Pharm. and Exp. Therapeutics* 268(1):380–387.

Rollema, H. et al., "Comparison of the effects of intracerebrally administered $MPP^+$ (1–methyl–4–phenylpyridinium) in three species: microdialysis of dopamine and metabolites in mouse, rat and monkey striatum," (1989) *Neuroscience Letters* 106:275–281.

Roos, R.A. et al., "Response fluctuations in Parkinson's disease," (1990) *Neurology* 40(9):1344–1346.

Schapira, A.H., "Oxidative stress in Parkinson's disease," (1995) *Neuropathol. Appl. Neurobiol.* 21(1):3–9.

Spencer, J.P.E. et al., "Superoxide–dependent depletion of reduced glutathione by L–DOPA and dopamine. Relevance to Parkinson's disease," (1995) *NeuroReport* 6:1480–1484.

Sperber, K. et al., "Hydroxychloroquine treatment of patients with human immunodeficiency virus type 1," (1995) *Clinical Therapeutics* 17(4):622–636.

Springer, C. et al., "Chloroquine treatment in desquamative interstitial pneumonia," (1987) *Archives of Disease in Childhood* 62:76–77.

Stepien, K.B. and Wilczok, T., "Studies of the mechanism of chloroquine binding to synthetic DOPA–melanin," (1982) *Biochem. Pharmacol.* 1;31(21):3359–3365.

Stoof, J.C. et al., "Leads for the development of neuroprotective treatment in Parkinson's disease and imaging methods for estimating treatment efficacy," (1999) *Eur. J. Pharmacol.* 375(1–3):75–86.

Swaiman, K.F. and Machen, V.L., "Chloroquine reduces neuronal and glial iron uptake," (1986) *J. Neurochemistry* 46(2):652–654.

Tipton, K.F. and Singer, T.P., "Advances in our understanding of the mechanisms of the neurotoxicity of MPTP and related compounds," (1993) *J. Neurochem.* 61(4):1191–1206.

Tjalve, H. et al., "Studies on the binding of chlorpromazine and chloroquine to melanin in vivo," (1981) *Biochem. Pharmacol.* 30(13):1845–1847.

Toole–Simms, W. et al., "Transplasma membrane electron and proton transport is inhibited by chloroquine," (1990) *Biochem. International* 21(4):761–769.

Vainshtok, A.B., "Treatment of Parkinsonism with delagil," (1972) *Klin. Med (Mosk)* 50(9):51–56.

Yong, V.W. et al., "Depletion of glutathione in brainstem of mice caused by N–methyl–4–phenyl–1,2,3,6–tetrahydropyridine is prevented by antioxidant pretreatment," (1986) *Neuroscience Letters* 63:56–60.

Youdim, M.B.H. et al., "Is Parkinson's disease a progressive siderosis of substantia nigra resulting in iron and melanin induced neurodegeneration?", (1989) *Acta Neurol. Scand.* 126:47–54.

*Biochemistry*, (1975) Lubert Stryer, Stanford University, W.H. Freeman and Company, San Francisco, CA.

*Clinical Toxicology of Commercial Products* (1984) Gosselin, Smith, Hodge, 5$^{th}$ Ed., Williams & Wilkins, Baltimore/London, II–245.

*Diagnostic Clinical Neuropsychology* (1997) Bigler, E. and Clement, P., 3$^{rd}$ E., Universtity of Texas Press, Austin, TX.

*Fundamentals of Anatomy & Physiology* (1995) Martini, Frederic H., 3$^{rd}$ Ed., Prentice Hall, Englewood Cliffs, NJ.

*The Merck Index*, (1996) 12$^{th}$ Ed., Susan Budavari, Ed., Merck Research Laboratories, Inc., Whitehouse Station, NJ, "Chloroquine—7–chloro–4–(4–diethylamino–1 methylbutylamino)quinoline," p. 2220.

*The Merck Index*, (1960) 7$^{th}$ Ed., P.G. Stecher, Ed., Merck & Co., Inc. Rahway, NJ.

*Organic Chemistry*, (1996) McMurry, John, 4$^{th}$ Ed., Brooks/Cole Publishing, an International Thomson Publishing Co., Pacific Grove, CA.

*Physicians' Desk Reference*, (1996) 50$^{th}$ Ed., Medical Economics Company, Inc., Montvale, NJ.

*Physicians' Desk Reference*, (2000) 54$^{th}$ Ed., Medical Economics Company, Inc., Montvale, NJ.

"Practical chemotherapy of Malaria," (1990) World Health Org. Technical Report Series No. 805, p. 141.

*Russian Drug Index*, 2d Ed., S. Jablonski, US Dept. HEW, Public Health Service Publication No. 814 (Revised 1967).

*Textbook of Medical Physiology* (1996) Guyton, A.C. and Hall, J.E., 9$^{th}$ Ed., W.B. Saunders Company, Philadelphia, PA.

Augustijns, P. et al., "Stereoselective de–ethylation of chloroquine in rat liver microsomes," (1999) *Eur. J. Drug Metabolism & Pharmacokinetics* 24(1):105–108 (abstract only).

Augustijns, P. and Verbeke, N., "Stereoselective pharmacokinetic properties of chloroquine and de–ethyl–chloroquine in humans," (1993) *Clin. Pharmacokinetics* 24(3):259–269 (abstract only).

Begley, D.J., "The blood–brain barrier: principles for targeting peptides and drugs to the central nervous system," (1996) *J. Pharm. Pharmacol.* 48(2):136–146.

De Boer, A.G. and Breimer, D.D., "The blood–brain barrier: clinical implications for drug delivery to the brain," (1994) *J. R. Coll. Physicians Lond.* 28(6):50–506.

De Boer, A.G. and Breimer, D.D., "The blood–brain barrier: clinical implications for drug delivery to the brain," (1994) *J. R. Coll. Physicians Lond.* 28(6):50–506.

Donatelli, P. eta l., "Stereoselective inhibition by chloroquine of histamine N–methyltransferase in the human liver and brain," (1994) *Eur. J. Clin. Parmacol.* 47(4):345–349 (abstract only).

Ducharme, J. et al., "Enantioselective disposition of hydroxychloroquine after a single oral dose of the racemate to healthy subjects," (1995) *Brit. J. Clin. Pharmacol.* 40(2):127–133 (abstract only).

Ducharme, J. and Farinotti, R., "Clinical pharmacokinetics and metabolism of chloroquine. Focus on recent advances," (1996) *Clin. Pharmacokinet.* 31(4):257–74 (abstract only).

Scaria, P.V. et al., "Differential binding of the enantiomers of chloroquine and quinacrine to polynucleotides: implications for steroselective metabolism," (1993) *Biopolymers* 33(6):887–95 (abstract only).

Tago, C.N. and Ofori–Adjei, D., "Effects of chloroquine and its enantiomers on the development of rat embryos in vitro," (1995) *Teratology* 52(3):137–142 (abstract only).

Yatin, S.M. et al., "Alzheimer's amyloid beta–peptide associated free radicals increase rat embryonic neuronal polyamine uptake and ornithine decarboxylase activity: protective effect of vitamin E," (1999) *Neuroscience Letters* 263(1):17–20 (abstract only).

\* cited by examiner

CHLOROQUINE DERIVATIVES FOR THE TREATMENT OF PARKINSON'S DISEASE

This application takes priority from U.S. patent application Ser. No. 60/143,767 filed Jul. 13, 1999, U.S. patent application Ser. No. 60/175,051 filed Jan. 7, 2000, and U.S. patent application Ser. No. 60/202,140 filed May 5, 2000, which are incorporated herein by reference to the extent not inconsistent herewith.

BACKGROUND

Idiopathic Parkinson's Disease (IPD) is a progressive neurodegenerative disorder. The onset of IPD symptoms begin to manifest when a threshold reduction of 60%–70% nigral neurons accompanied by an 80%–90% attenuation in striatal dopamine efflux, has been reached (Koller, W. C., "When does Parkinson's disease begin?", (1992) *Neurology* 42(S4):27–31). Symptoms include tremor, postural imbalance, rigidity, bradykinesia and akinesia (*Diagnostic Clinical Neuropsychology*, Bigler, E. and Clement, P., Eds., 3$^{rd}$ Ed. 1997). These symptoms intensify as the disease progresses. In severe stages of IPD, following the onset of akinesia, even the simplest movements require a monumental degree of concentration and mental effort, often to the point of anguish (*Textbook of Medical Physiology*, Guyton, A. C. and Hall, J. E., Eds., 9$^{th}$ Ed., W. B. Saunders Company, Philadelphia, Pa., 1996). IPD is also characterized by a number of autonomic (Vainshtok, A. B., "Treatment of Parkinsonism with delagil," (1972) *Klin. Med* (*Mosk*) 50(9): 51–56) and non-motor symptoms including depression (Cummings, J. L., "Depression and Parkinson's Disease: A Review," (1992) *Am. J. Psychiatry* 149(4):443–454) and frontal lobe dysfunction (Gotham, A. M. et al., "Levodopa treatment may benefit or impair 'frontal' function in Parkinson's disease," (1986) *Lancet* 25;2(8513):970–971).

In the United States, it is estimated that 5–24 in every 100,000 people suffer from IPD, with the majority of low income cases going undiagnosed (Chrischilles, E. A. et al., "The health burdens of Parkinson's disease," (1998) *Movement Disorders* 13(3):406–413 ). In 1995, the World Health Organization conducted a global epidemiological evaluation of the incidence of IPD, showing a worldwide incidence of 5.32 per 100,000 people with an astounding incidence rate of 49.33 per 100,000 people over the age of 65 (M. Privett, WHO). Although more recent epidemiological figures are unavailable, in 1996 with the world population being approximately 5.7 billion, an estimated 2.8 million people had a confirmed diagnosis of IPD.

Current pharmacological treatments for IPD and other Parkinsonian-like motor disorders include anticholinergic agents, catechol-o-methyltransferase inhibitors and dopaminergic agents (Physicians' Desk Reference, 2000, 54$^{th}$ Ed., Medical Economics Company, Inc., Montvale, N.J.). Since the late sixties, dopamine precursor L-DOPA, has been employed for the symptomatic relief of IPD motor dysfunction (Mena, M. A. et al., "Pharmacokinetics of L-DOPA in patients with Parkinson's disease," (1986) *Advances in Neurology* 45:481–486). However, following long term use of L-DOPA (generally 5–8 years), diminished therapeutic efficacy is observed in approximately 50% of IPD patients (Roos, R. A. et al., "Response fluctuations in Parkinson's disease," (1990) *Neurology* 40(9): 1344–1346). A wearing off of L-DOPA efficacy precedes the development of serious motor side effects such as on/off motor oscillations and dyskinesias (Carlsson, Arvid, "Development of new pharmacological approaches in Parkinson's disease," (1986) *Advances in Neurology* 45:513–518). Further, when medications are increased to compensate for the development of these new motor dysfunctions, more serious side effects are generally observed, including psychiatric complications, while producing only minimal therapeutic benefit (Stoof, J. C. et al., "Leads for the development of neuroprotective treatment in Parkinson's disease and imaging methods for estimating treatment efficacy," (1999) *Eur. J. Pharmacol.* 375(1–3):75–86).

Deprenyl, a monoamine oxidase (MAO) B inhibitor, was the first drug suggested to provide causal treatment of Parkinson's Disease by alleviating symptoms and attenuating the progression of the illness (Mytilineou, C. et al., "L-(-)-desmethylselegiline, a metabolite of selegiline [L-(-)-deprenyl], protects mesencephalic dopamine neurons from excitotoxicity in vitro," (1997) *J. Neurochemistry* 68(1):434–436). However, there remains much controversy regarding the therapeutic efficacy of Deprenyl. While some physicians prefer to prescribe Deprenyl when patients first present with symptoms of Parkinson's Disease (Goldstein, M. and Lieberman, A., "The role of the regulatory enzymes of catecholamine synthesis in Parkinson's disease," (1992) *Neurology* 42(S4):8–12), other physicians dispute claims of neural protection (Olanow, C. W. and Calne, D., "Does selegiline monotherapy in Parkinson's disease act by symptomatic or protective mechanisms?" (1992) *Neurology* 42(S4):13–26).

Poewe and Wenning (Poewe, W. H. and Wenning, G. K., "The natural history of Parkinson's disease," (1998) *Annals of Neurology* 44(S1):S1–S9) reviewed several longitudinal studies which evaluated Parkinson's Disease medications. The Parkinson's Research Group of the United Kingdom found that when Deprenyl was co-administered with L-DOPA, a 60% increase in patient mortality was observed, compared to the group being treated with L-DOPA only. Deprenyl is now rarely prescribed by European physicians for the treatment of IPD. In contrast, American researchers determined that Deprenyl is capable of delaying the need to commence L-DOPA treatment for a period of up to nine months. However, no neural protection was found in two-year patient follow-up examinations (Poewe and Wenning, 1998, supra). In Parkinson's Disease the average lifespan is 9.4 years following an initial diagnosis. Further, the onset of gait disorders is closely associated with mortality rate. To be superior to current causal treatments (i.e—Deprenyl), a pharmacological treatment must: a) prolong the need to commence L-DOPA for more than nine months; b) retain efficacy beyond a two-year period; and, c) prevent, delay, or otherwise alleviate gait disorders.

Up to 20% of the people initially diagnosed with IPD, actually suffer from atypical IPD (APD), striatonigral degeneration (SND), or multiple symptom atrophy (MSA) (Antonini, A. et al., "Differential diagnosis of Parkinsonism with [$^{18}$F]Fluorodeoxyglucose and PET," (1998) *Movement Disorders* 13(2):268–274). Little or no response to conventional Parkinson's Disease drug therapy is usually the differentiating factor between a diagnosis of APD, SND and MSA as opposed to IPD (Dethy, S. et al., "Asymmetry of basal ganglia glucose metabolism and dopa responsiveness in Parkinsonism," (1998) *Movement Disorders* 13(2): 275–280). Often, little can be done for people suffering these atypical afflictions. Therefore, it would be of great benefit if a pharmacological means were identified that could alleviate symptoms of atypical Parkinson's Disease, as well as IPD.

The exact cause or causes of IPD are still unknown. Nonetheless, scientists have discovered a multitude of pathological abnormalities in the Parkinsonian brain. These findings include but are not limited to: a) toxic metabolite formation during neuromelanin (NM) synthesis (Graham, D. G., "Autoxidation versus covalent binding of quinones as the mechanism of toxicity of dopamine, 6-hydroxydopamine, and related compounds toward C1300 neuroblastoma cells in vitro" (1978) *Molecular Pharmacology* 14:644–653); b) heightened affinity of endogenous and exogenous toxins for NM (Tipton, K. F. and Singer, T. P., "Advances in our understanding of the mechanisms of the neurotoxicity of MPTP and related compounds," (1993) *J. Neurochem*. 61(4):1191–1206); c) mitochondrial impairment (Mizuno, Y. et al., "Mitochondrial dysfunction in Parkinson's disease," (1998) *Annals of Neurology* 44(S1): S99–S109); d) increased oxidative stress potentiated by reduced levels of antioxidants (Merad-Boudia, M. et al., "Mitochondrial impairment as an early event in the process of apoptosis induced by glutathione depletion in neuronal cells: relevance to Parkinson's disease," (1998) *Biochem. Pharmacology* 56:645–655); e) protein oxidation and lipid peroxidation (Jenner, P. et al., "Understanding cell death in Parkinson's disease," (1998) *Annals of Neurology* 44(1): S72–S84); f) augmented iron content and abnormal Fe(II)/Fe(III) ratios (Riederer, P. et al., "Transition metals, ferritin, glutathione, and ascorbic acid in Parkinsonian brains," (1989) *J. Neurochemistry* 52(2):515–520); and g) the accumulation of extracellular protein peptide fragments (Loo, D. T. et al., "Apoptosis is induced by β-amyloid in cultured central nervous system neurons," (1993) *Proc. Natl. Acad. Sci. USA* 90:7951–7955). An example of these extracellular amyloid peptide fragments are the non-Aβ components in Lewy bodies (Culvenor, J. G. et al., "Non-Aβ component of Alzheimer's disease amyloid (NAC) revisited," (1999) *Am. J. Pathology* 155:1173–1181) which trigger an apoptotic cascade. Taken individually, these pathological findings would not pose a tremendous cellular threat. Collectively and occurring simultaneously, they serve to progressively annihilate the melanized catecholamine neurons residing in the mesencephalon, ultimately producing the classic signs of Parkinson's Disease.

Chloroquine Compounds

Chloroquine [7-chloro-4-(4-diethylamino-1-methylbutylamino)quinoline] (*The Merck Index*, p. 2220, 1996) is a synthetically manufactured anti-malarial containing the quinoline nucleus. Chloroquine was developed over fifty years ago. It continues to be the most widely employed drug for the treatment of the asexual erythrocytic form of *P. falciparum* (Deepalakshmi, P. D. et al., "Effect of chloroquine on rat liver mitochondria," (1994) *Indian J. Exp. Biology* 32(11):797–799). Unfortunately, due to widespread use of chloroquine, treatment resistant stains of malaria, first reported in 1961, continue to emerge globally, making the use of chloroquine obsolete in many regions (Bitonti, A. J. et al., "Reversal of chloroquine resistance in malaria parasite *Plasmodium falciparum* by desipramine," (1988) *Science* 241:1301–1303). A number of chloroquine derivates have been identified for antimalarial and other use. See U.S. Pat. Nos. 5,948,791, 5,834,505, 5,736,557, 5,639,737, 5,624,938, 5,596,002 and 4,421,920.

Due to the widespread use of chloroquine, a number of beneficial therapeutic properties and medicinal applications, outside of conventional malarial treatment, have been identified. Most of the following studies employed chloroquine phosphate.

Chloroquine phosphate is a potent inhibitor of acid chondromucoprotease present in cartilage and of cathepsin B1, a protease especially important in the initiation of proteolysis (De Duve, C. et al., "Lysosomotropic agents," (1974) *Biochem. Pharm*. 23:2495–2531). These properties have rendered chloroquine phosphate useful in the treatment of rheumatoid arthritis (*Clinical Toxicology*, supra, Section III, pp. 355–362). Further, chloroquine phosphate is known to reduce hypertension (*Physician's Desk Reference*, pp. 2301–2302, 1996). Chloroquine phosphate and other 4-aminoquinoline compounds have been prescribed for the treatment of cardiac arrhythmia (*Clinical Toxicology*, supra, Section III, pp. 355–362). A version of antimalarial drug called Cardioquin® is produced by the Purdue Fredrick Company for the maintenance of sinus rhythm after conversions from atrial fibrillation (*Physician's Desk Reference*, pp. 2521–2522, 2000). Chloroquine phosphate also targets malignant metastatic melanomas that generally bear an accumulation of melanin. The utilization of chloroquine phosphate for the treatment of these tumors is limited by the lack of accumulation in the amelanotic forms that readily manifest (Lindquist, N. G., "Accumulation of drugs on melanin," (1973) *Acta Radiol. Diag. (Stockholm)* 325:1–92). A more recent application of chloroquine phosphate is to suppress the human immunodeficiency virus type 1 (HIV-1) replication in vivo within T-cells and monocytes (Sperber, K. et al., "Hydroxychloroquine treatment of patients with human immunodeficiency virus type 1," (1995) *Clinical Therapeutics* 17(4):622–636; Ornstein, M. H. and Sperber, K., "The anti-inflammatory and antiviral effects of hydroxychloroquine in two patients with acquired immunodeficiency syndrome and active inflammatory arthritis," (1996) *Arthritis Rheum*. 39(1):157–161).

The above medicinal applications of chloroquine phosphate are generally known to those practicing medicine in the USA. The following applications of chloroquine phosphate have been discovered and successfully employed by doctors throughout the world. Chloroquine phosphate has been used to treat renal disorders such as glomerulonephritis and amyloidosis, with observed improvement in renal function and attainment of various lengths of remission (Makarenko, I. E. and Levitsky, E. P., "Resoquin in the clinic of internal illnesses, and the possible side effects of its use," (1950). A randomized trial of the prolonged use of chloroquine phosphate to treat advanced pulmonary sarcoidosis, suggests that patients responded better to chloroquine phosphate and withstood medication side effects better than with conventional corticosteroids (Baltzan, M. et al., "Randomized trial of prolonged chloroquine therapy in advanced pulmonary sarcoidosis," (1999) *Am. J. Respir. Crit. Care Med*. 160:192–197). Conditions of acute hypertension can benefit from the administration of chloroquine phosphate, which acts as a vasodilator without depressing cardiac contractibility (Abiose, A. K. et al., "Chloroquine-induced venodilation in human hand veins," (1997) *Clin. Pharm. & Therapeutics* 61(6):677–683). Chloroquine phosphate inhibits lysosomal proteolysis in vitro, and has been suggested to be a useful agent in counteracting protein wasting observed in several catabolic diseases (De Feo, P. et al., "Chloroquine reduces whole body proteolysis in humans," (1994) *Am. J. Physiology* 267:E183–E186). Chloroquine phosphate inhibits the biological availability of iron and has been suggested as advantageous for the treatment of iron-loading disorders (Legssyer, R. et al., "Effect of chronic chloroquine administration on iron loading in the liver and reticuloendothelial system and on oxidative responses by the alveolar macrophages," (1999) *Biochem. Pharmacology* 57(8): 907–91 1). Several case histories have been published regarding the efficacy in administering chloroquine phosphate to infants suffering from desquamative interstitial pneumonitis who presented with failure to thrive, tachypnea and hypoxia (Springer, C. et al., "Chloroquine treatment in desquamative interstitial pneumonia," (1987) *Archives of Disease in Childhood* 62:7677), and were non-respondent to steroids (Leahy, F. et al., "Desquamative interstitial pneumonia responsive to chloroquine," (1985) *Clinical Pediatrics* 24(4):230–232).

Further recognized, but non-FDA approved, uses of chloroquine phosphate include treatments for: cholera, idiopathic pulmonary hemosiderosis, lupus erythematosus, lymphoid interstitial pneumonitis, onchocerca volvulus, porphyria cutanea tarda, m. sarcoidosis, and ulcerative colitis (MICROMEXEX®, 2000, available: http//phamtom.uchsc.edu/mdxcgi/di). U.S. Pat. No. 5,430,039 suggests the use of chloroquine to inhibit neuronal cell death resulting from a calcium-related disorder of the central or peripheral nervous system, erroneously characterizing Parkinson's Disease as such a disorder. Vainshtok, A. B., "Treatment of Parkinsonism with delagil," (1972) *Klin. Med (Mosk)* 50(9):51–56, reports administration of Delagil, a chloroquine compound or analog (exact compound unknown) to a group of medication-free patients (dosage unknown) suffering symptoms related to Parkinson's disease with moderate to dramatic response.

Enantiomers of Chloroquine

Chloroquine and hydroxychloroquine are racemic mixtures of (−)- and (+)-enantiomers. The (−)-enantiomers are also known as (R)-enantiomers (physical rotation) and l-enantiomers (optical rotation). The (+)-enantiomers are also known as (S)-enantiomers (physical rotation) and r-enantiomers (optical rotation). The (+)-enantiomer metabolizes peripherally about eight times more rapidly than the (−)-enantiomer, producing toxic metabolites including de-ethyl chloroquine (Augustijins, P. and Verbeke, N. [1993] "Stereoselective pharmacokinetic properties of chloroquine and de-ethyl chloroquine in humans," *Clinical Pharmacokinetics* 24(3):259–69; Augustijins, P. et al. [1999], "Stereoselective de-ethylation of chloroquine in rat liver microsomes," *Eur. J. Drug Metabolism & Pharmacokinetics* 24(1):105–8; DuCharme, J. and Farinotti R. [1996], "Clinical pharmacokinetics and metabolism of chloroquine," *Clinical Pharmacokinetics* 31(4):257–74). Administering (+)-chloroquine may cause cardiac side effects due to toxic metabolite formation. The (−)-enantiomer has a longer half-life and lower clearance than the (+)-enantiomer (Ducharme, J. et al. (1995), "Enantio-selective disposition of hydroxychloroquine after a single oral dose of the racemate to healthy subjects," *British J. Clinical Pharmacology* 40(2): 127–33). The enantiomers of chloroquine and hydroxychloroquine may be prepared by procedures known to the art.

All publications referred to herein are incorporated by reference to the extent not inconsistent herewith.

SUMMARY OF THE INVENTION

This invention provides compositions and methods for increasing cellular respiration of melanized catecholamine neurons such as dopamine neurons in the substantia nigra, epinephrine and norepinephrine neurons, of protecting such neurons against oxidative degradation, and for treatment of Parkinson's Disease, including both alleviation of symptoms and preventing onset or progression of symptoms. The compositions of this invention may be administered long-term. The compositions of this invention are also useful for preventing on-off syndrome, a condition in which L-Dopa and other dopamine agonists temporarily or permanently lose their ability to ameliorate the symptoms of Parkinson's Disease after an initial period of effectiveness.

The term "CQ" includes chloroquine (7-chloro-4-(4-diethylamino-1-methylbutylamino)quinoline), chloroquine phosphate (7-chloro-4-(4-diethylamino-1-methylbutylamino)quinoline phosphate, and hydroxychloroquine (7-chloro-4-(4-diethylamino-1-methylbutylamino) quinoline), and mixtures thereof. Similarly, the terms (−)-chloroquine and (+)-chloroquine include (−)- and (+)-chloroquine phosphate and (−)- and (+)-hydroxychloroquine respectively.

Compositions useful for increasing cellular respiration of melanized catecholamine neurons, and/or alleviating, preventing or halting progress of Parkinson's symptoms comprise neuromelanin-binding chloroquine analogs and derivatives containing a quinoline nucleus, preferably selected from the group consisting of:

7-chloro-4-(4-diethylamino-1-methylbutylamino) quinoline (chloroquine);

7-hydroxy-4-(4-diethylamino-1-methylbutylamino) quinoline; chloroquine phosphate;

7-chloro-4-(4-diethylamino-1-butylamino)quinoline (desmethylchloroquine);

7-hydroxy-4-(4-diethylamino-1-butylamino)quinoline;

7-chloro-4-(1-carboxy-4-diethylamino-1-butylamino) quinoline;

7-hydroxy-4-(1-carboxy-4-diethylamino-1-butylamino) quinoline;

7-chloro-4-(1-carboxy-4-diethylamino-1-methylbutylamino)quinoline;

7-hydroxy-4-(1-carboxy-4-diethylamino-1-methylbutylamino)quinoline;

7-chloro-4-(4-ethyl-(2-hydroxyethyl)-amino-1-methylbutylamino)quinoline (hydroxychloroquine);

7-hydroxy-4-(4-ethyl-(2-hydroxyethyl)-amino-1-methylbutylamino)quinoline; hydroxychloroquine phosphate;

7-chloro-4-(4-ethyl-(2-hydroxyethyl)-amino-1-butylamino)quinoline (desmethylhydroxychloroquine);

7-hydroxy-4-(4-ethyl-(2-hydroxyethyl)-amino-1-butylamino)quinoline;

7-chloro-4-(1-carboxy-4-ethyl-(2-hydroxyethyl)-amino-1-butylamino)quinoline;

7-hydroxy-4-(1-carboxy-4-ethyl-(2-hydroxyethyl)-amino-1-butylamino)quinoline;

7-chloro-4-(1-carboxy-4-ethyl-(2-hydroxyethyl)-amino-1-methylbutylamino)quinoline;

7-hydroxy-4-(1-carboxy-4-ethyl-(2-hydroxyethyl)-amino-1-methylbutylamino)quinoline;

8-[(4-aminopentyl)amino]-6-methoxydihydrochloride quinoline;

1-acetyl-1,2,3,4-tetrahydroquinoline; 8-[4-aminopentyl) amino]-6-methoxyquinoline dihydrochloride;

1-butyryl-1,2,3,4-tetrahydroquinoline; 7-chloro-2-(o-chlorostyryl)-4-[4-diethylamino-1-methylbutyl] aminoquiinoline phosphate;

3-chloro-4-(4-hydroxy-α,α'-bis(2-methyl-1-pyrrolidinyl)-2,5-xylidinoquinoline, 4-[(4-diethylamino)-1-methylbutyl)amino]-6-methoxyquinoline;

3,4-dihydro-1 (2H)-quinolinecarboxyaldehyde;

1,1'-pentamethylenediquinoleinium diiodide; and 8-quinolinol sulfate, enantiomers thereof, said compounds covalently linked or complexed or mixed with targeting agents, and mixtures thereof, as well as suitable pharmaceutical salts thereof. Chloroquine and hydroxychloroquine are preferred; (−)-enantiomers thereof are more preferred, and said compounds covalently linked or complexed or mixed with targeting agents are most preferred. Neuromelanin-binding compounds such as chlorpromazine and other antipsychotics which bind to dopamine receptors are not included within the scope of PD-effective neuromelanin-binding compounds of this invention. Any chloroquine analog or derivative known to the art and capable of binding neuromelanin may be useful in the methods of this invention.

Preferably the neuromelanin-binding compound is selected from the group consisting of compounds capable of crossing the blood-brain barrier in effective amounts. Such compounds include those which are more lipophilic, are capable of changing to effective chirality after crossing the blood-brain barrier, have side chain substituents which enhance compound transport via blood-brain barrier transporter mechanisms, or are complexed or covalently linked with antibodies or other targeting moieties, or administered in combination with other compounds facilitating their crossing the blood-brain barrier, as known to the art. The (−)-enantiomer of chloroquine (referred to herein as the active enantiomer) is preferred.

In a preferred embodiment, the compositions useful for increasing cellular respiration of melanized catecholamine neurons comprise an effective amount of a composition comprising (−)-CQ or (−)-CQ mixed, complexed or covalently linked with a targeting agent; an amount of (+)-CQ less than that of said (−)-CQ or (−)-CQ complexed or covalently linked with a targeting agent; and a suitable pharmaceutical carrier.

A targeting agent is a substance that when complexed with the CQ helps carry it across the blood brain barrier. Preferred targeting agents are lipophilic moieties known to the art which are attached to the active molecule at a position which does not interfere with the ability of the quinoline ring to bind to neuromelanin, and antibodies such as an antibody capable of binding to the transferrin receptor on brain capillary cells, e.g., as described in U.S. Pat. No. 6,015,555, incorporated herein by reference to the extent not inconsistent herewith.

Such compositions containing (−)-chloroquine may include anywhere from no (+)-CQ to about 49% (+)-CQ. An amount of (+)-CQ sufficient to bind to enzymes causing peripheral breakdown of CQ is preferred, leaving more of the (−)-CQ to cross the blood brain barrier where its therapeutic effect takes place. Preferably the compositions comprise between about 10% and about 20% (+)-CQ.

In one embodiment, a single adult dosage amount of said composition effective for increasing cellular respiration of melanized catecholamine neurons is provided, preferably less than an antimalarial single adult dosage amount, more preferably less than about 1 mM base equivalent, and most preferably less than about 0.5 mM base equivalents of CQ. As is known to the art, the term "base equivalents" refers to amount of active ingredient (e.g., in reference to chloroquine phosphate, refers to the chloroquine minus the phosphate and filler components). A single adult dosage amount with respect to use for alleviation, preventing or stopping progression of symptoms of Parkinson's Disease or for other uses will be an amount effective when administered daily to provide the stated therapeutic effect.

Compositions of this invention may also comprise an effective amount of at least one adjuvant selected from the group consisting of antioxidants, retinal protective agents, other neural protective compounds, dopamine or dopamine agonists, and free radical deactivators. The antioxidant may be any antioxidant known to the art to prevent free radical formation and oxidative degradation of tissues and is preferably selected from the group consisting of probucol, pyncnogenol, Vitamin C, Vitamin E, superoxide dismutase, preferably synthetic, BHT, BHA, and melatonin. The retinal protective agent is preferably a composition administered locally to prevent binding of retinal melanin with the CQ, as is known to the art, e.g., alkanes and alcohols of $C_1$–$C_4$, and ginko biloba. The neural protective compound is any compound known to the art and preferably is selected from the group consisting of selegiline hydrochloride and other monoamine oxidase inhibitors. The dopamine agonist is any compound known to the art as an anti-Parkinson's treatment and preferably is selected from the group consisting of L-DOPA, pramipexole, ropinerole, bromocriptine, tolcapone, and carbidopa. The free radical deactivator is any compound known to the art and preferably is selected from the group consisting of superoxide dismutase, selegiline, hydrochloride, and tolcapone.

This invention also provides kits comprising in close proximity, such as in a container or blister pack, effective dosage amounts and forms of the compositions of this invention for single doses, or doses per week, or other appropriate time period, preferably in combination with an adjuvant, such as an antioxidant, dopamine or dopamine agonist, or other adjuvant as discussed above suitable for co-administration with said composition, in effective dosage forms and amounts.

Suitable pharmaceutical carriers are known to the art and include carriers aiding in transport across the blood/brain barrier, such as nanoparticles onto which the compositions are absorbed, coated with a detergent, e.g., as described in Begley, D. J. (1996) "The blood-brain barrier: principles for targeting peptides and drugs to the central nervous system," *J. Pharm. Pharmacol.* 48(2):136–46, incorporated herein by reference to the extent not inconsistent herewith.

This invention also provides methods for increasing cellular respiration of melanized catecholamine neurons, and methods for alleviating symptoms or stopping appearance and/or progression of symptoms of Parkinson's Disease, and methods for preventing symptoms of on-off syndrome associated with treatment with dopamine or a dopamine agonist of a patient suffering symptoms of a disease selected from the group consisting of idiopathic and atypical Parkinson's disease, conditions characterized by nigrostriatal degeneration, multiple system atrophy, and vascular Parkinson's Disease, said methods comprising administering to said patient an effective amount of the above composition of this invention. The methods are suitable for any mammal having such melanized neurons or symptoms of Parkinson's Disease. Methods for treating or preventing symptoms of Parkinson's Disease also comprise identifying patients having such symptoms or at risk of developing them.

Further provided are methods of making pharmaceutical compositions effective for increasing cellular respiration of melanized catecholamine neurons comprising: providing a compound or complex of this invention as described above, providing a suitable pharmaceutical carrier; and mixing said compound or complex and pharmaceutical carrier to form a composition effective to increase cellular respiration of melanized catecholamine neurons.

Instead of mixing (+)-CQ with (−)-CQ, the method of making the compositions of this invention comprising (−)-CQ may be practiced by starting with racemic chloroquine and removing an amount of (+)-CQ to leave a CQ composition effective to increase cellular respiration of melanized catecholamine neurons.

DETAILED DESCRIPTION

The term "increasing cellular respiration" means measurably increasing oxygen consumption, increasing aerobic cellular respiration and reducing anaerobic cellular respiration, e.g., as measured by lactate in the cerebral spinal fluid.

The term "diminishing oxidative degradation of dopamine neurons in the substantia nigra" means measurably diminishing such degradation as measured by assays known to the art, including measures of free iron ion availability and oxygenated radical formation.

The term "Parkinson's Disease" as used herein includes idiopathic Parkinson's Disease (IPD), atypical Parkinson's Disease (APD), striatonigral degeneration (SND), multiple symptom atrophy (MSA), and vascular Parkinson's Disease.

The term "alleviating symptoms of Parkinson's Disease" means measurably reducing, inhibiting, attenuating and/or compensating for at least one symptom of Parkinson's disease, such as tremor, postural imbalance, rigidity, bradykinesia, akinesia, gait disorders, and on/off fluctuations. These symptoms may result from toxic metabolite formation during neuromelanin (NM) synthesis, heightened affinity of endogenous and exogenous toxins for NM, mitochondrial impairment, increased oxidative stress potentiated by reduced levels of antioxidants, protein oxidation and lipid peroxidation, augmented iron content and abnormal Fe(II)/Fe(III) ratios, and the accumulation of extracellular protein peptide fragments, which conditions may also be alleviated by the compositions of this invention.

The compositions of this invention containing (−)-CQ should have more (−)-CQ or (−)-CQ mixed, complexed or covalently linked with a targeting agent than (+)-CQ because the toxic metabolites of (+)-CQ make it less suitable for long-term use, and the better melanin-binding properties of (−)-CQ, its longer half life, and lower clearance make it more effective for long-term administration (e.g. at least about six weeks, more preferably, about two years, and most preferably, at least about ten years or more).

An effective amount of the compositions of this invention is an amount necessary to produce a measurable effect. For example, an effective amount of the compositions of this invention to increase cellular respiration measurably increases cellular respiration by assays known to the art as discussed above. In compositions containing (−)-CQ, the effect may be produced by the (−)-CQ, or partially by the (−)CQ and partially by (+) CQ. Similarly, an effective amount of a composition of this invention to alleviate or stop the progression of symptoms of Parkinson's Disease is an amount which does so based on art-known tests such as the Unified Parkinson's Disease Rating Scale and the Tinetti Gait and Balance Assessment Tool, comparing symptoms of treated patients with symptoms of the same patients prior to and/or after treatment, or with symptoms of untreated patients at the same stage of Parkinson's Disease.

Preventing symptoms of Parkinson's Disease includes identifying patients at risk for developing such symptoms. Identification of patients susceptible to onset of Parkinson's Disease may be done by genetic testing, prediction from family history or other means known to the art such as PET scans. When symptoms of Parkinson's do not develop, or do not develop to the expected (average) degree, they are considered to have been prevented by the methods and compositions of this invention.

Preventing on-off symptoms in patients being treated with L-Dopa or like medications means measurably stopping or decreasing such symptoms as compared with patients at similar stages of Parkinson's Disease being treated with such medications.

The compounds of this invention may formulated neat or may be combined with one or more pharmaceutically acceptable carriers for administration. For example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solution or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular mixture employed, the mode of administration and the severity of the condition being treated. However, in general, satisfactory results are obtained when the compounds of the invention are administered at a daily adult dosage of from about 0.5 to about 1000 mg, optionally given in divided doses two to four times a day, or in sustained release form. For most large mammals the total daily dosage is from about 1 to 1000 mg, preferably from about 2 to 500 mg. Dosage forms suitable for internal use comprise from about 0.5 to 1000 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation. Preferably a single daily adult dose comprises less than about 1 mM, and more preferably less than about 0.5 mM base equivalents, more preferably less than about 1 mM, and more preferably less than about 0.5 mM base equivalents.

The compounds of this invention may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred. In some cases it may be desirable to administer the compounds to the patient's airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

"Suitable pharmaceutical carriers" as referred to herein include distilled and pharmaceutical grade water but do not include water or buffers unsuitable for administration to a human patient.

There are several mechanisms by which neuromelanin may contribute to symptoms of Parkinson's disease by contributing to formation of toxic products including superoxide and hydroxy radicals, which catalyze lipid peroxidation, and oxidation of NADH resulting in disruption of the neuron's respiration and reducing the amount of energy available to the neurons via aerobic respiration.

Neuromelanin can be considered a waste product of catecholamine degradation and gradually accumulates within the cytosol of catecholamine neurons throughout one's lifetime. Dopamine is autoxidized to cytotoxic and reactive oxygenated species such as 6-hydroxydopamine (6-OHDA) and semiquinone radicals. Low glutathione levels contribute to oxidative stress in Parkinson's disease, and allow available hydrogen peroxide to be further catalyzed by iron into highly toxic superoxide radicals and hydroxyl radical species as well as semiquinone radicals. Dopamine and L-DOPA interaction with superoxide radicals augments depletion of glutathione, leading to a downward spiral of detrimental reactions.

Monoamine oxidase forms toxic metabolites from a number of substances such as beta-carboline derivatives and tetrahydroisoquinoline which are present in excessive amounts in the cerebral spinal fluid of people with Parkinson's Disease. These toxic metabolites have high affinity to neuromelanin, and once bound may cause almost complete arrest of ATP production, resulting in impaired respiration, loss of energy available to the neurons and massive melanized cell loss which leads to symptoms of Parkinson's Disease. Inhibitors of monoamine oxidase B such as Deprenyl prevent formation of these toxic metabolites. Iron also tends to bind to neuromelanin, resulting in a cascade of pathogenic reactions leading to neuronal death. Increasing iron concentrations in basal ganglia are observed with normal aging, and in patients with Parkinson's Disease, iron is pathologically elevated with high ferric/ferrous ion ratios. The ferric ions contribute, with 6-OHDA, to the formation of harmful superoxide and hydroxyl radicals leading to lipid peroxidation and cell breakdown.

Iron chelators have been shown to reverse impaired mitochondrial respiration caused by 6-OHDA inhibition of NADH dehydrogenase. 6-OHDA catalyzes the release of iron from intracellular ferritin stores which in turn catalyzes lipid peroxidation. This toxic chain of events can be inhibited by superoxide dismutase. Both iron chelators and chloroquine phosphate have been found to limit the availability of free iron, so that it is not available to catalyze these toxic reactions.

The iron transporter protein, diferric transferrin, which delivers iron throughout the body also contributes to loss of energy available to the neurons by interfering with availability of reduced NADH. Chloroquine phosphate has been found to inhibit intracellular oxidation of NADH by melanin.

Chloroquine phosphate binds to neuromelanin and does not inhibit enzymatic synthesis of iron into biologically essential compounds. It not only prevents incorporation of iron into neurons, but also inhibits and release of iron from intracellular iron pools. In addition chloroquine phosphate has been found to heighten an astrocytic immune response against accumulation of extracellular protein deposits in the brain contributing to Alzheimer's Disease.

The (−) isomer of chloroquine is an even more effective neuromelanin binders than racemic chloroquine because it breaks down less peripherally, has a longer half-life and lower clearance, and so is more available to cross the blood brain barrier, as well as having a stabilizing effect on DNA. It is therefore preferred for use in this invention.

EXAMPLES

Example 1

Enantiomers of chloroquine phosphate were isolated according to the procedure of Stalcup, A. M. et al. (1996), *Analytical Chemistry* 68:2248–50. Comparisons of these enantiomers with respect to ability to inhibit diamine oxidase and bind to neuromelanin are performed in vitro. Results show significantly enhanced ability of the active enantiomer in both assays to inhibit diamine oxidase and bind neuromelanin.

Example 2

A within-subjects, open labeled, parallel study is performed to evaluate the efficacy of CQ and enantiomeric CQ (test compounds) for the treatment of motor disorders in adults having a diagnosis of Idiopathic Parkinson's Disease (IPD) and Symptomatic Parkinson's Disorders, using the Unified Parkinson's Disease Rating Scale and the Tinetti Gait and Balance Assessment Tool for assessment pretreatment, during treatment, and two weeks post-treatment. The treatment period assesses the safety and durability of response for up to eight weeks. An initial two-week pretreatment period establishes each participant's baseline neurophysiological and well-being being measures. A final evaluation, administered following a two-week treatment withdrawal period, evaluates each participant for symptom restoration.

Thirty adults 30–75 years of age, including fifteen subjects having a confirmed diagnosis of stage I–III IPD, designated Group I, and 15 subjects having a diagnosis of Symptomatic Parkinson's Disorders resultant from vascular disorders, multi-infarct state, hypoxia, normal pressure hydrocephalus and/or postencephalitis, designated Group II, receive a reverse titration of the test medication during the first week of treatment. This is followed by a one-time-per-day maintenance dose of 155 mg per day taken with the evening meal.

During the initial 24-hour treatment period, subjects are instructed to take 155 mg of the test medication four times per day. On study days 2 and 3, subjects are instructed to take 155 mg of test medication 3 times per day. On study days 4, 5 and 6, subjects are instructed to take 155 mg of test medication 2 times per day. On study day 7, subjects are instructed to take 155 mg of the test medication daily with their final meal of the day. On treatment day 10, physicians determine final maintenance dose to be taken each evening with the subject's final meal of the day for the duration of the treatment period. The maintenance dose may be kept at 155 mg test medication per day or adjusted to a lower or higher dose, e.g. down to 100 mg if the subject is showing improvement but having gastrointestinal or other discomforts. The dose is increased up to 200 mg or 255 mg per day if the subject has not experienced symptom relief.

Improvements in pre-treatment (baseline) scores on the above-described or similar measuring instruments, and/or decline in function and score values following the medication withdrawal period are used for assessment. Subjects are checked for the occurrence of adverse events during the study three times per week. Laboratory evaluations (chemistry and hematology profiles) are performed at pre-treatment screening and during the treatment period on days 10, 28 and 56, and also during the two-week post-treatment exit evaluation.

Pre-treatment (baseline) measurements are taken on three separate occasions, at three different times of the day, morning, noon and evening, during the initial two-week pre-treatment evaluation period. The pre-treatment scores are averaged to determine each patient's baseline neurophysiological and well-being measurements. Five separate neurophysiological and well-being evaluations are administered on treatment days 7, 14, 28, 42 and 56. Medication is discontinued immediately after the neurophysiological and well-being evaluation administered on treatment day 56. Patients are seen for one additional exit interview including complete neurophysiological, well-being, and laboratory evaluations two weeks after the experimental treatment is discontinued.

Baseline (averaged scores) obtained during the two-week pre-treatment period are compared to scores obtained during treatment days 7, 14, 28, 42 and 56 to determine any changes in patient status throughout the treatment period. The final two-week post-treatment evaluation scores are used to determine a lingering of effect by comparing the two week post-treatment evaluation scores to the pre-treatment baseline measurements. Improvement of motor symptoms from pre-treatment, during treatment and post-treatment are evaluated, as well as improved well-being. Within-group improvement scores are analyzed using a t-test of differences for scores from the pre-test condition to the post-test condition using a p value of 0.05. Variables are summarized by treatment group according to subgroups of gender, race, and age. Treatment groups are further compared using the Cochran-Mantel-Haenszel test with stratifications by the above variables.

Changes from pre-treatment evaluations to days 7, 14, 28, 42 and 56 in each clinical sign and symptom are summarized by treatment group. The two treatment groups are compared with respect to the percentage of subjects who showed either resolution or improvement in the signs and symptoms among the subjects presenting with the signs and symptoms using Fisher's exact test. Potentially clinically significant laboratory values and mean changes from baseline of vital signs data are summarized within both treatment groups. Times to resolution/improvement of symptoms after treatment are also summarized by treatment group and compared using the log rank test. Subject satisfaction data and subject symptoms collected from questionnaires are also summarized by treatment group and analyzed. Based on an adverse event rate of 3%, the treatment group sizes used provide approximately 80% power to detect significance difference at the 0.05 (two-tailed) significance level.

Significant improvement in symptoms and halting of progression of symptoms both during and post-treatment is observed.

While the invention has been described in specific terms, it is not to be limited to the description but is to be afforded the full scope of the appended claims and all equivalents thereto. For example, other neuromelanin-binding compounds and complexes containing the quinoline ring structure known to the art are equivalent to those specifically described, as are other modifications to the compositions to enhance crossing the blood/brain barrier, biological half-life, or other desirable properties.

What is claimed is:

1. A composition useful for increasing cellular respiration of melanized catecholamine neurons comprising a compound selected from the group consisting of chloroquine, chloroquine phosphate, hydrochloroquine, and enantiomers thereof, covalently linked, mixed or complexed with a brain-targeting agent, acceptable pharmaceutical salts thereof, and mixtures of the foregoing.

2. A composition of claim 1 wherein said compound comprises:
   an effective amount of (−)-CQ;
   an amount of (+)-CQ less than that of said (−)-CQ wherein the amount of said (+)-CQ is from about 0% to about 20% of the total (+)-CQ and (−)-CQ; and
   a suitable pharmaceutical carrier.

3. The composition of claim 2 wherein said CQ is chloroquine.

4. The composition of claim 2 wherein said CQ is chloroquine phosphate.

5. The composition of claim 2 wherein said CQ is hydroxychloroquine.

6. The composition of claim 2 wherein said (−)-CQ is covalently linked with an antibody to transferrin.

7. The composition of claim 2 wherein said (−)-CQ is covalently linked with a lipophilic moiety.

8. The composition of claim 1 consisting of a single dosage amount for administration to an adult human less than an antimalarial single adult dosage amount of said composition, effective for increasing cellular respiration of melanized catecholamine neurons, said single dosage amount for administration to an adult human being less than about 1 mM base equivalents.

9. The composition of claim 8 wherein said single dosage amount is an amount less than an antimalarial single adult dosage amount, and is less than about 0.5 mM base equivalents.

10. The composition of claim 1 also comprising an effective amount of an adjuvant selected from the group consisting of antioxidants, retinal protective agents, other neural protective compounds, dopamine and dopamine agonists, and free radical deactivators.

11. The composition of claim 10 wherein said adjuvant is an antioxidant selected from the group consisting of probucol, pyncnogenol, Vitamin C, Vitamin E, butylated hydroxytoluene (BHT), butylated hydroxyanisole (BHA), melatonin, and superoxide dismutase.

12. A method of making a pharmaceutical composition effective for increasing cellular respiration of melanized catecholamine neurons comprising:
   (a) providing a neuromelanin-binding agent selected from compounds of the group consisting of chloroquine, chloroquine phosphate, hydroxychloroquime, and enantiomers thereof, said compounds being mixed, complexed or covalently bonded with a brain-targeting agent, acceptable pharmaceutical salts thereof and mixtures of the foregoing;

(b) providing a suitable pharmaceutical carrier; and (c) mixing the materials of steps (a) and (b) to form a composition effective to increase cellular respiration of melanized catecholamine neurons.

13. The method of claim 12 wherein said neuromelanin-binding agent is (−)-CQ.

14. The method of claim 13 also comprising providing (+)-CQ and mixing said (+)-CQ with said (−)-CQ, wherein the amount of said (+)-CQ is from about 0% to about 20% of the total (+)-CQ and (−)-CQ, and said pharmaceutical carrier.

15. The method of claim 12 comprising the step of mixing said neuromelanin-binding agent with a brain targeting agent.

16. A composition useful for treatment of Parkinson's disease comprising a compound selected from the group consisting of chloroquine, chloroquine phosphate, hydroxychloroquine, and enantiomers thereof, covalently linked, mixed or complexed with a brain targeting agent, acceptable pharmaceutical salts thereof, and mixtures of the foregoing.

17. The composition of claim 16 wherein said compound comprises:

an effective amount of (−)-CQ;

an amount of (+)-CQ less than that of said (−)-CQ wherein the amount of said (+)-CQ is from about 0% to about 20% of the total (+)-CQ and (−)-CQ; and a suitable pharmaceutical carrier.

* * * * *

UNITED STATES PATENT AND TRADEMARK OFFICE
CERTIFICATE OF CORRECTION

PATENT NO. : 6,417,177 B1
APPLICATION NO. : 09/615639
DATED : July 9, 2002
INVENTOR(S) : Jodi Nelson Page 1 of 1

It is certified that error appears in the above-identified patent and that said Letters Patent is hereby corrected as shown below:

In the Claims:

Claim 1 at column 14, line 19, replace "hydrochloroquine" with "hydroxychloroquine"

Signed and Sealed this

Thirtieth Day of December, 2008

JON W. DUDAS
*Director of the United States Patent and Trademark Office*